(12) United States Patent
Jayaraman et al.

(10) Patent No.: US 6,970,731 B1
(45) Date of Patent: Nov. 29, 2005

(54) FABRIC-BASED SENSOR FOR MONITORING VITAL SIGNS

(75) Inventors: Sundaresan Jayaraman, Atlanta, GA (US); Sungmee Park, Tucker, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

(21) Appl. No.: 09/713,161

(22) Filed: Nov. 14, 2000

Related U.S. Application Data

(63) Continuation-in-part of application No. 09/273,175, filed on Mar. 19, 1999, now Pat. No. 6,381,482, and a continuation-in-part of application No. 09/157,607, filed on Sep. 21, 1998, now Pat. No. 6,145,551.

(51) Int. Cl.[7] ................................................. A61B 5/04
(52) U.S. Cl. ....................... 600/388; 600/390; 600/393
(58) Field of Search ............................... 600/372, 386, 600/388, 389, 390, 393–395

(56) References Cited

U.S. PATENT DOCUMENTS

| | | | | |
|---|---|---|---|---|
| 710,429 | A | * | 10/1902 | Collins et al. ............. 607/149 |
| 2,579,383 | A | | 12/1951 | Goudsmit |
| 2,935,096 | A | | 5/1960 | Cole |
| 3,020,935 | A | | 2/1962 | Balis |
| 3,409,007 | A | | 11/1968 | Fuller |
| 3,534,727 | A | * | 10/1970 | Roman ..................... 600/389 |
| 3,542,010 | A | * | 11/1970 | Love ........................ 600/384 |
| 4,016,868 | A | * | 4/1977 | Allison ..................... 600/388 |
| 4,102,331 | A | * | 7/1978 | Grayzel et al. ........... 600/385 |
| 4,299,878 | A | | 11/1981 | Rheaume |
| 4,506,673 | A | * | 3/1985 | Bonnell .................... 607/50 |
| 4,572,197 | A | | 2/1986 | Moore et al. |
| 4,580,572 | A | | 4/1986 | Granek et al. |
| 4,606,968 | A | | 8/1986 | Thornton et al. |
| 4,668,545 | A | | 5/1987 | Lowe |
| 4,727,603 | A | | 3/1988 | Howard |
| 4,848,351 | A | * | 7/1989 | Finch ........................ 600/391 |
| 5,103,504 | A | | 4/1992 | Dordevic |
| 5,143,089 | A | * | 9/1992 | Alt ............................ 607/121 |
| 5,212,379 | A | | 5/1993 | Nafarrate et al. |
| 5,316,830 | A | | 5/1994 | Adams, Jr. et al. |
| 5,374,283 | A | * | 12/1994 | Flick |
| 5,415,204 | A | | 5/1995 | Kitamura |
| 5,436,444 | A | | 7/1995 | Rawson |
| 5,507,290 | A | * | 4/1996 | Kelly et al. ............... 600/393 |
| 5,592,977 | A | | 1/1997 | Kikuchi et al. |
| 5,624,736 | A | | 4/1997 | DeAngelis et al. |
| 5,636,378 | A | | 6/1997 | Griffith |
| 5,694,645 | A | | 12/1997 | Triplette |
| 6,080,690 | A | * | 6/2000 | Lebby et al. ............. 442/209 |
| 6,145,551 | A | * | 11/2000 | Jayaraman et al. ....... 139/387 |
| 6,151,528 | A | * | 11/2000 | Maida ....................... 607/149 |
| 6,210,771 | B1 | * | 4/2001 | Post et al. ................. 428/100 |

* cited by examiner

*Primary Examiner*—Lee S. Cohen
(74) *Attorney, Agent, or Firm*—Thomas, Kayden, Horstemeyer & Risley LLP; Todd Deveau

(57) ABSTRACT

The present invention comprises a fabric-based sensor for monitoring vital signs or other electrical impulses of a subject. The sensor is woven or knitted from conductive fibers and, when in contact with the body, receives signals from the wearer and transmits them to a processing or monitoring device through a data-output terminal. The sensor may be integrated into the fabric of a garment or used independently as a conductive patch. Additionally, the sensor may provide bi-directional communication by both monitoring electrical impulses and sending them.

23 Claims, 4 Drawing Sheets

Novel Fabric-based Sensors

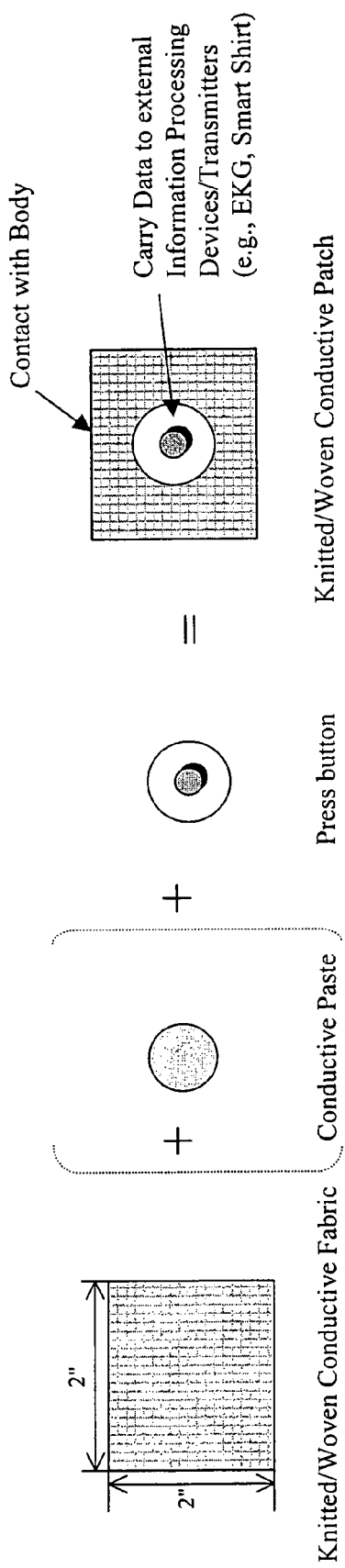
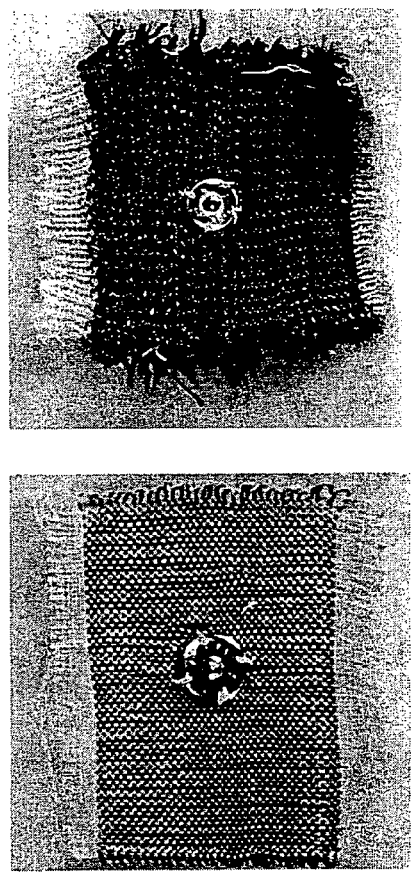
Figure 1. Novel Fabric-based Sensors

Front View

To Monitoring Equipment

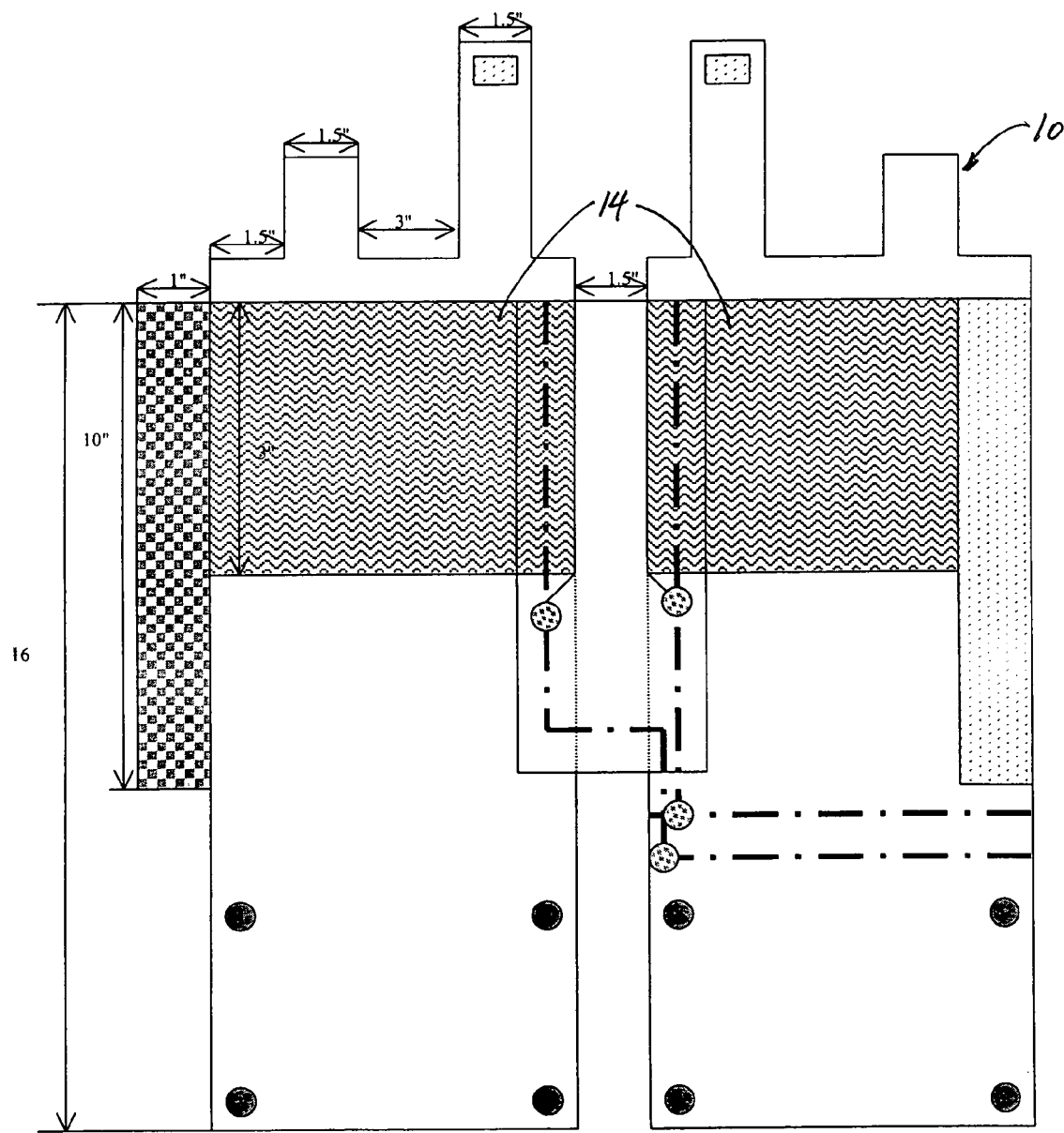
Figure 3 Opened Out View and Details

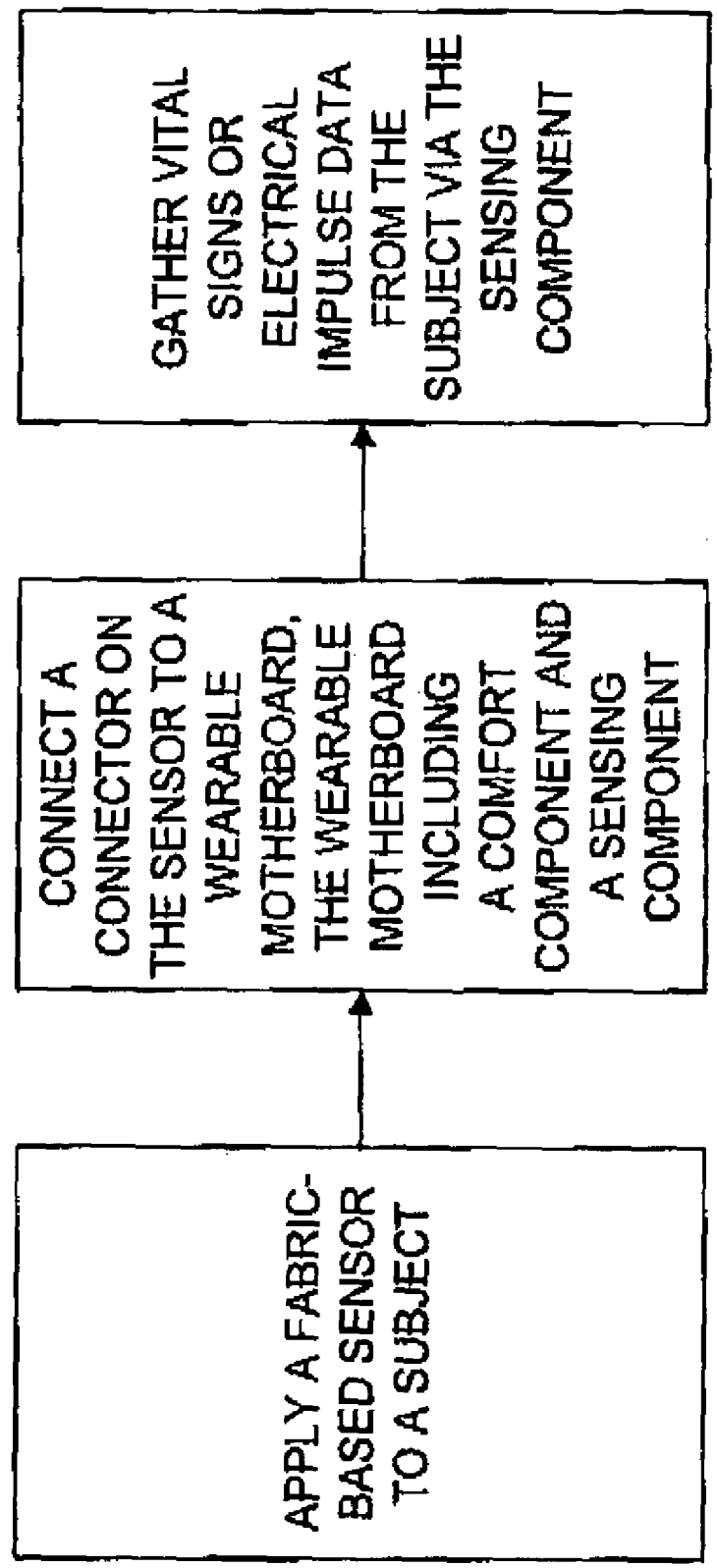

FABRIC-BASED SENSOR FOR MONITORING VITAL SIGNS

This application is a continuation-in-part of U.S. Ser. No. 09/157,607, filed on Sep. 21, 1998, now U.S. Pat. No. 6,145,551, and is a continuation-in-part U.S. Ser. No. 09/273,175, filed on Mar. 19, 1999, now U.S. Pat. No. 6,381,482.

BACKGROUND OF THE INVENTION

1. Field of the Invention

The present invention relates to a fabric-based sensor for monitoring vital signs or other electrical impulses of a subject. The sensor is woven or knitted from conductive fibers and, when in contact with the body, is capable of receiving signals from the wearer and transmitting them to a processing or monitoring device through a data-output connection or terminal. The sensor may be integrated into a garment or used as independently as a conductive patch, and it may provide bi-directional communication by sending electrical impulses back to the subject.

2. Background of the Art

Conventional medical electrodes are used for sensing electrical transmission between the surface of a subject's skin and electrical leads connected to monitoring equipment. Typically, the electrodes use an adhesive backing to affix the conductive lead to the subject's skin. A conductive gel is often used to enhance electrical transmission.

Many of the existing sensors are either rubberized electrodes or gel-based sensors that stick to the body of the subject. Both types of sensors have the major drawbacks of being difficult to remove and causing skin irritation and chafing.

U.S. Pat. Nos. 4,722,354 and 5,450,845 to Axelgaard describe an electrical stimulation electrode which integrates conductive fibers with pre-wired, hard-wired electrical leads into a flexible electrode patch. The flexible patch allows for greater patient comfort and movement, without disruption of the electrode placement. The patch described by Axelgaard consists of several layers, including a non-conductive layer, an adhesive layer and the conductive fiber layer.

Co-pending application U.S. Ser. No. 09/157,607, filed on Sep. 21, 1998, now U.S. Pat. No. 6,145,551 to Jayaraman, et al., incorporated herein by reference in its entirety as if fully set forth herein, discloses a process for the production of a woven garment which can accommodate armholes and which may also incorporate conductive fibers integrated into the woven fabric by one weaving process. The garment produced by the Jayaraman process is capable of collecting data from several different types of sensors attached thereto, and transmitting the data through a single connector, such as a snap T-connector.

Additionally, co-pending application U.S. Ser. No. 09/273,175, filed on Mar. 19, 1999 by Jayaraman et al., now U.S. Pat. No. 6,381,482, and incorporated by reference in its entirety as if fully set forth herein, discloses a fabric or garment which includes an integrated information infrastructure for collecting, processing, transmitting and receiving information. The garment functions as a "wearable motherboard," which, by utilizing the interconnection of electrical conductive fibers, integrates many data-collecting sensors into the garment without the need for multiple stand-alone wires or cables. The information may be transmitted to several monitoring devices through a single electronic lead or transceiver.

There exists a need in the art for a flexible electrode which can adhere to the subject without the need for pain-causing adhesive. The present invention is directed to a conductive fabric sensor which does not include multiple layers such as the Axelgaard electrode and, when in contact with the body, picks up electrical signals from the wearer. Utilizing the weaving technique and the interconnection of electrical conductive fibers of the co-pending Jayaraman application and the Jayaraman patent, it is possible to produce a comfortable fabric-based sensor which is very light weight and does not require hard wiring or adhesives.

SUMMARY OF THE INVENTION

It is, therefore, an object of the present invention to provide a fabric-based sensor for monitoring vital signs and other electrical impulses of a subject, which sensor does not require the use of adhesives.

It is a further object of the invention to provide a garment having at least one fabric-based sensor for monitoring vital signs and other electrical impulses of a subject, wherein the sensor is knitted or woven within the garment and does not need to be attached as a separate component to the garment by hard-wiring or by a connector such as a snap connector.

It is still another object of the present invention to provide a fabric-based sensor capable of bi-directional communication.

One innovative facet of the present invention is the ability to monitor vital signs and other electrical impulses using a fabric patch woven or knitted from conductive fibers, which patch eliminates the need for adhesives to position an electrode on the subject. The conductive fabric may be used alone or it may be integrated into a garment containing other fibers. Additionally, the conductive patch may be used to send and receive electrical impulses to and from a remote source.

In a first embodiment, a fabric-based sensor for monitoring vital signs and other electrical impulses of a subject is provided. The sensor is made from knitted or woven non-insulated, conductive fibers attached to a data-output terminal, for example a snap connector. The fabric is directly contacted with a subject's skin, eliminating the need for a backing material or conductive gel, although conductive paste may optionally be used. The sensor directly contacts the skin, receiving the electrical signals and transmitting them to the data-output terminal, which relays the signals to a monitoring device. Optionally, the fabric-based sensor may include a conductive paste between the sensor and the data-output terminal. The sensor may be plugged into the connectors of the "wearable motherboard" described in U.S. Pat. No. 6,381,482 or to other monitoring devices.

In a further embodiment, a garment having at least one fabric-based sensor for monitoring vital signs and other electrical impulses of a subject, wherein the sensor is knitted or woven integrally within the garment is provided. By knitting or weaving a conductive fiber integrally into a fabric, a garment may be created entirely out of the conductive fibers or may have one or more distinct patches of the conductive fabric. A conductive patch or conductive patches, comprised of the woven or knitted conductive fibers and a data-output terminal, optionally with conductive paste, may be incorporated into the garment at positions necessary to obtain a desired signal. For example, several conductive patches may be knitted or woven or sewn into a shirt at positions appropriate for obtaining pulse or temperature.

These readings are obtained from the fibers, transmitted to the connectors and then transmitted to a monitor or other processor for interpretation.

In another embodiment, a conductive fabric patch for providing bi-directional communication to and from a subject is provided. The fabric-based sensor of the present invention, used either independently or incorporated integrally into a garment, may be used to transmit vital signs and other electrical impulses from the subject to a monitoring source. Additionally, the conductive patch may receive electrical signals from an external source. The patch may be used to provide an electrical charge to a subject, for example, an electric shock to a baby with apnea.

It can be seen from the description herein of our invention that a fabric-based sensor made of conductive fibers is provided, which can be incorporated into a full-fashioned woven or knitted garment, which can be used for monitoring vital signs or sending electrical pulses to the subject. These and other objects and advantages of the present invention will become apparent upon reading the following specification and claims in conjunction with the accompanying drawing figures.

BRIEF DESCRIPTION OF THE DRAWINGS

FIG. 1 illustrates the design of the fabric-based sensor of the present invention, showing both a woven conductive patch and a knitted conductive patch.

FIG. 3 illustrates an opened view and details of a garment having a fabric-based sensor integrated therein.

FIG. 4 illustrates a flow chart diagram of a method for monitoring the vital signs or other electrical data impulses of a subject.

DETAILED DESCRIPTION OF THE ILLUSTRATIVE EMBODIMENT

A. The Fabric-Based Sensor

Figure 2:
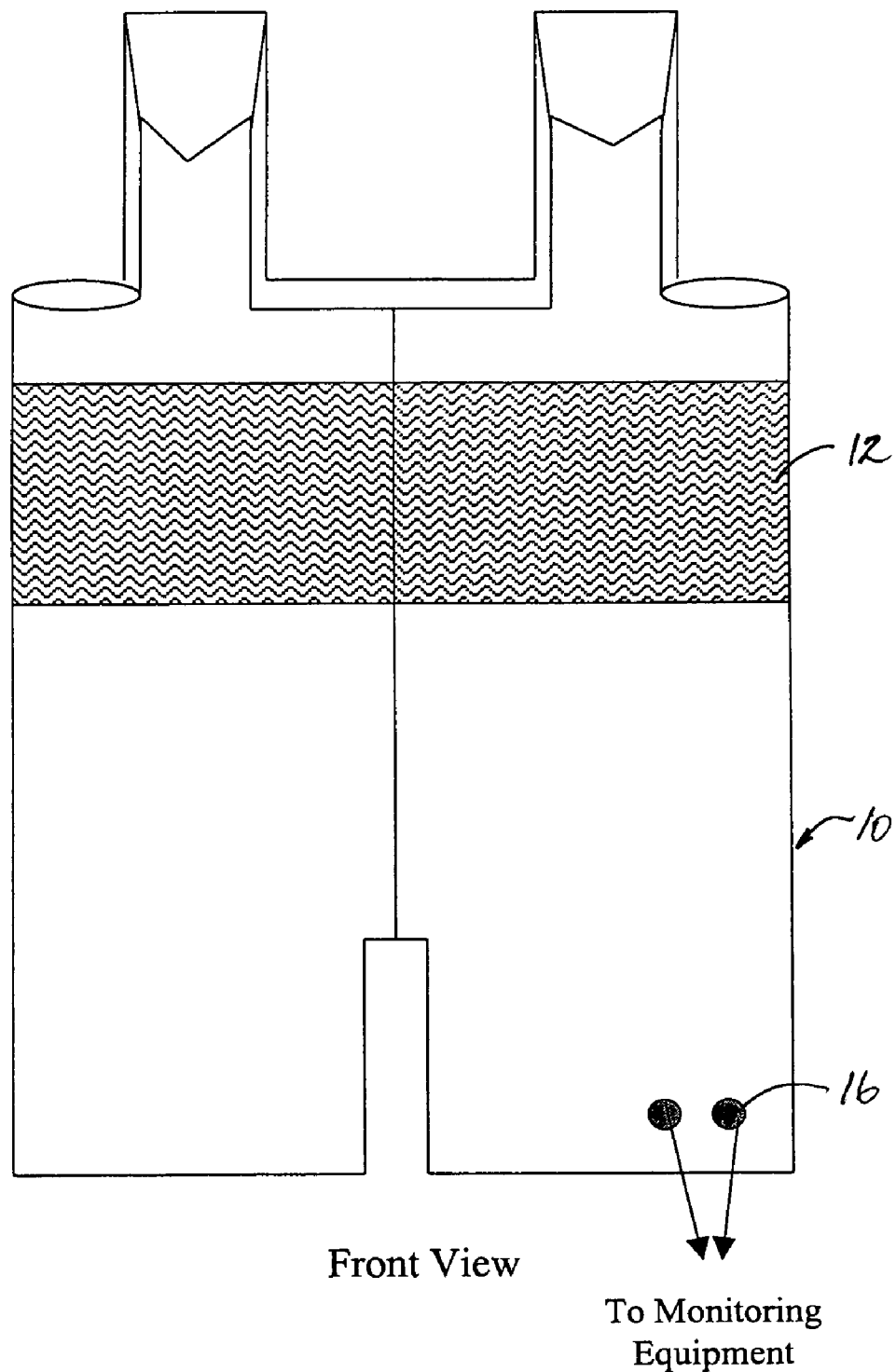
FIG. 2 illustrates a front view of a garment having a fabric-based sensor integrated therein.

As illustrated in FIG. 1, a fabric-based sensor for monitoring vital signs and other electrical impulses of a subject is provided. The sensor is made from knitted or woven non-insulated, conductive fabric attached to a data-output terminal, for example a snap connector. The sensor may optionally contain conductive gel. The fabric is directly contacted with a subject's body, eliminating the need for a backing material or adhesive. The sensor directly contacts the skin, receiving the electrical signals and transmitting them to the data-output terminal, which relays the signals to a monitoring device or other information processing device.

Conductive fabric sensors can be incorporated into fabric by any conventional method, for example by knittng or weaving. Sensors can be made from other types of conducting fibers, depending on fabric densities and structures.

1. Knitted Fabric Sensor

Any yarn applicable to conventional knitted fabrics may be incorporated with conductive fibers into the conductive fabric sensor of the present invention. The choice of material for the non-conductive yarn will ordinarily be determined by the end use of the fabric and will be based on a review of the comfort, fit, fabric hand, air permeability, moisture absorption and structural characteristics of the yarn. Suitable yarns include, but are not limited to, cotton, polyester/cotton blends, microdenier polyester/cotton blends and polypropylene fibers such as MERAKLON (made by Dawtex Industries).

The table provided below shows the parameters used for producing the knitted fabric sensor embodiment of the present invention. The information provided is exemplary only, and is not intended to limit the scope of the present invention.

| Knitted Fabric Sensor | |
|---|---|
| Material | Uninsulated 100% Stainless Steel Yarn |
| Part # | VN 12/1 X 275/100Z/316L |
| Source | Bekaert Corporation |
| Yarn Size | 2250 Denier |
| Fabric Structure | 1 × 1 Rib |
| Fabric Density | 16 Wales/Inch and 18 Courses/Inch |
| Sensor Size | 1.5" × 1.5" |
| Sensor Weight | 12 oz/yd$^2$ |

2. Woven Fabric Sensor

The table provided below shows the parameters used for producing the woven fabric sensor embodiment of the present invention. The information provided is exemplary only, and is not intended to limit the scope of the present invention.

| Woven Fabric Sensor | |
|---|---|
| Material for Warp | Cotton |
| Yarn Size (Warp) | 18s Ne |
| Material for Filling (Weft) | Uninsulated 100% Stainless Steel Yarn |
| Yarn Size (Weft) | 2250 Denier |
| Filling Yarn Part # | VN 12/1 X 275/100Z/316L |
| Filling Yarn Source | Bekaert Corporation |
| Fabric Structure | 1 × 1 Plain |
| Fabric Density | 30 Ends/Inch and 22 Picks/Inch |
| Sensor Size | 1.5" × 1.5" |
| Sensor Weight | 7.5 oz/yd$^2$ |

Additionally, electrical conductive fiber can be used in place of the cotton fiber material for the warp fiber of the above embodiment.

3. Conductive Fibers

Electrical conducting fibers for the fabric sensor include, but are not limited to: (i) doped inorganic fibers; (ii) stainless steel fibers; and (iii) thin gauge copper wires. All of these fibers can readily be incorporated into the fabric sensor. An example of an available conducting fiber is uninsulated X-Static from Squat Industries, Scranton, Pa. An example of an available thin copper wire is 24 gauge insulated copper wire from Ack Electronics, Atlanta, Ga.

One example of a highly conductive yarn suitable for incorporation into the fabric sensor of the present invention is Bekinox available from Bekaert Corporation, Marietta, Ga., a subsidiary of Bekintex Nev., Wetteren, Belgium, which is made up of stainless steel fibers and has a resistivity of 60 ohm-meter. The bending rigidity of this yarn is comparable to that of the polyamide high-resistance yarns and can be easily incorporated. The electrical conductive fiber used in the woven or knitted sensor should preferably be uninsulated.

4. Other Fabrics Useful in the Sensor of the Present Invention

Fabrics having form-fitting properties and high comfort properties may also be used in the fabric sensor of the present invention. The form-fitting component keeps the sensor in place on the subject's body during movement, eliminating the need for adhesive. The material usually has a high degree of stretch to provide the required form-fit.

A preferred form-fitting fabric is SPANDEX fiber, a block polymer with urethane groups. Its elongation at break ranges from 500 to 600% and, thus, can provide the necessary form-fit. Its elastic recovery is also extremely high (99% recovery from 2–5% stretch) and its strength is in the 0.6–0.9 grams/denier range. It is resistant to chemicals and withstands repeated washings. SPANDEX fibers can be obtained from E.I. du Pont de Nemours, Wilmington, Del.

The form-fitting component can take the form of a strap or wrap or other component in conjunction with the woven or knitted fabric sensor into which the form-fitting fiber is integrated in order to hold the sensor in the desired place on the body. Alternatively, where the sensor is integrated within the garment fabric itself, as illustrated in FIGS. 2 and 3, or attached to the garment in the form of a sensor patch by, for example, T-connectors, the form-fitting component can be incorporated into the garment itself to hold the sensor patch in the desired location. In this latter case, the form-fitting component can be woven or knitted into the garment fabric, as described in co-pending U.S. Ser. No. 09/273,175, filed on Mar. 19, 1999.

B. Garment Containing Fabric-Based Sensor

As illustrated in FIGS. 2 and 3, the fabric-based sensor 12 described above can be incorporated into a garment, wherein the sensor is itself knitted or woven integrally within the garment fabric 10 to provide monitoring of vital signs or other electrical impulses. By knitting or weaving a conductive fiber into a fabric, a garment may be created entirely out of the conductive fibers or have one or more distinct patches 14 of the conductive fabric. A conductive patch or conductive patches, comprised of the woven or knitted conductive fibers and a data-output terminal 16, optionally with conductive paste, may be incorporated into the garment at positions necessary to obtain a desired signal. For example, several conductive patches may be incorporated into a garment by any known method, including knitting, weaving or sewing. Incorporation into a garment may be at selective positions optimal for obtaining pulse or temperature readings. These readings are obtained from the conductive fibers, transmitted to the connectors and then transmitted to a monitor or other processor for interpretation.

Garments may be fashioned from any conventional knitting, weaving or sewing process. Patches containing the fabric-based sensors of the present invention may be incorporated into the garment by any known technique, including, but not limited to sewing, knitting, weaving, gluing, VELCRO, etc. The patches may be strategically placed to monitor whatever vital sign is contemplated, and several patches may be incorporated into a single garment to monitor different vital signs or electrical impulses.

Garments contemplated by the present invention include, but are not limited to shirts, dresses, pants, undergarments, hats, gloves or other wearable items.

The garments can also be comprised of a form-fitting fiber component, as described above, which serves to secure the conductive fabric and the sensor to the body. The form-fitting fibers also serve to restrict movement of the sensors, thus assuring more consistent monitoring.

C. Sensor Providing Bi-Directional Communication

The fabric-based sensor of the present invention may be used to monitor vital signs or other electrical impulses from a subject. Additionally, the sensor may serve to deliver impulses to the subject from a remote source, thus providing bi-directional communication.

The sensor may be used to monitor respiration, pulse, temperature, EKG, EEG, or other electrical impulses. The fabric-based sensor, therefore, is useful in several medical applications, including but not limited to, continuously or intermittently monitoring (a) patients located nearby or at remote locations, (b) post-operative patients, (c) geriatric patients, mentally ill patients (for a better understanding of diseases such as chronic depression), (d) children susceptible to apnea and SIDS (sudden infant death syndrome), and (e) patients prone to allergic reactions (e.g., anaphylaxis reaction from bee stings).

In conjunction with the monitoring applications described above, the fabric-based sensor of the present invention may be used to send electrical impulses to the patient wearing the sensor. For example, when the sensor detects that a baby susceptible to SIDS has stopped breathing, a small electrical shock can be sent from a monitoring source to the child to stimulate breathing.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method for monitoring the vital signs of a subject comprising applying a fabric-based sensor to the subject and connecting the sensor to a monitor, the fabric-based sensor comprising:
   (a) a knitted or woven fully-conductive fabric including one or more individually conductive fibers integrated therein by the process of knitting or weaving the fabric, each conductive fiber being individually conductive prior to incorporation into the fabric in the absence of conductivity imparted to the fabric or to the fibers after incorporation into the fabric; and
   (b) an electrical lead for connection to a connector, the electrical lead being formed from one of the integrated individually conductive fibers; and
   (c) a connector connected to the electrical lead.

2. The method of claim 1, the fabric-based sensor having conductive paste between the electrical lead fiber and the connector.

3. The method of claim 2, wherein the fabric-based sensor is integrated into the fabric of a garment.

4. The method of claim 1, further comprising the step of providing an electrical impulse to said subject by connecting the connector to an impulse-delivering device, and delivering the impulse through the sensor to the subject.

5. The method of claim 4, the fabric-based sensor having conductive paste between the electrical lead fiber and the connector.

6. The method of claim 1, wherein the fabric-based sensor is integrated into the fabric of a garment.

7. A method for monitoring the vital signs or other electrical impulses of a subject comprising:
   applying a fabric-based sensor to the subject, the fabric-based sensor comprising:
      (a) a knitted or woven fully-conductive fabric including one or more individually conductive fibers integrated therein by the process of knitting or weaving the fabric, each conductive fiber being individually conductive prior to incorporation into the fabric in the absence of a conductive coating applied to the fabric or to the fibers; and
      (b) an electrical lead formed from one of the integrated individually conductive fibers;
   providing a wearable motherboard, wherein the wearable motherboard is a fabric comprising: a comfort component serving as the base of the fabric; and a sensing component integrated within said comfort component to form the fabric, wherein the sensing component includes an insulated electrical conductive component comprising one or more individually insulated conductive fibers the electrical lead of the fabric-based sensor being connected to the sensing component of the wearable motherboard; and gathering vital signs or electrical impulse data from the fabric-based sensor.

8. The method of claim 1, wherein the individually conductive fibers of the fabric-based sensor are knitted.

9. The method of claim 1, wherein the individually conductive fibers of the fabric-based sensor are woven.

10. The method of claim 7, wherein the individually conductive fibers of the fabric-based sensor are knitted.

11. The method of claim 7, wherein the individually conductive fibers of the fabric-based sensor are woven.

12. The method of claim 7, wherein the electrical lead of the fabric-based sensor is connected to the sensing component of the wearable motherboard by a connector.

13. The method of claim 12, wherein the fabric-based sensor and the wearable motherboard are integrated into the fabric of a garment.

14. The method of claim 7, further comprising connecting a monitor to either the fabric-based sensor or the wearable motherboard.

15. The method of claim 7, wherein the fabric-based sensor and the wearable motherboard are integrated into the fabric of a garment.

16. The method of claim 7, wherein the fabric-based sensor is separate from the wearable motherboard.

17. A method for monitoring the vital signs or other electrical impulses of a subject comprising:

applying a fabric-based sensor to the subject, the fabric-based sensor comprising:

a knitted or woven conductive fabric including one or more individually conductive fibers and non-conductive fibers integrated therein by the process of knitting or weaving the fabric, each conductive fiber being individually conductive prior to incorporation into the fabric in the absence of a conductive coating applied to the fabric or to the fibers;

providing a wearable motherboard, wherein the wearable motherboard is a fabric comprising: a comfort component serving as the base of the fabric; and a sensing component integrated within said comfort component to form the fabric, wherein the sensing component includes an insulated electrical conductive component comprising one or more individually insulated conductive fibers;

the fabric-based sensor being connected to the sensing component of the wearable motherboard; and gathering vital signs or electrical impulse data from the fabric-based sensor.

18. The method of claim 17, further comprising the step of connecting an impulse-delivering device to either the fabric-based sensor or to the sensing component of the wearable motherboard, and delivering an impulse to the subject.

19. The method of claim 17, wherein the individually conductive fibers of the fabric-based sensor are knitted.

20. The method of claim 17, wherein the individually conductive fibers of the fabric-based sensor are woven.

21. The method of claims 17, wherein the electrical lead of the fabric-based sensor is connected to the sensing component of the wearable motherboard by a connector.

22. The method of claim 17, wherein the fabric-based sensor and the wearable motherboard are integrated into the fabric of a garment.

23. The method of claim 17, wherein the fabric-based sensor is separate from the wearable motherboard.

* * * * *